United States Patent [19]
Brown et al.

[11] Patent Number: 6,031,103
[45] Date of Patent: Feb. 29, 2000

[54] PROCESS FOR MANUFACTURING 1-[3-CYCLOPENTYL -2(R)-[1(R)-HYDROXYCARBAMOYL)-2-(3, 4, 4-TRIMETHYL -2, 5-D IOXO-1-IMIDAZOLIDINYL) ETHYL] PROPIONYL] PIPERIDINE

[75] Inventors: Paul Anthony Brown, Hertfordshire, United Kingdom; Hans Hilpert, Reinach, Switzerland

[73] Assignee: Hoffmann-La Roche Inc., Nutley, N.J.

[21] Appl. No.: 09/296,749

[22] Filed: Apr. 22, 1999

Related U.S. Application Data

[62] Division of application No. 08/881,262, Jun. 24, 1997, abandoned.

[30] Foreign Application Priority Data

Jul. 4, 1996 [EP] European Pat. Off. .............. 96110814
Jan. 10, 1997 [EP] European Pat. Off. .............. 97100301

[51] Int. Cl.[7] ................................. C07D 211/14
[52] U.S. Cl. ................. 546/210; 548/319.1; 560/122
[58] Field of Search ............ 546/210; 548/319.1; 560/122

[56] References Cited

U.S. PATENT DOCUMENTS 5,614,625  3/1997  Broadhurst et al. .................... 540/480

FOREIGN PATENT DOCUMENTS 353 053   1/1990   European Pat. Off. .
676 404  10/1995   European Pat. Off. .
684 240  11/1995   European Pat. Off. .
95/33709 12/1995   WIPO .
99/03826  1/1999   WIPO .

OTHER PUBLICATIONS

K. Mikami et al., Org. Synth. 71, 14 (1993).
Mikami et al., "Asymmetric glyoxylate–ene reaction . . ." CA 110:113879 (1989).
Broadhurst et al "Hydroxyamic acid derivatives" CA 124:202261 (1995).
Mikami et al. "Asymmetric glyoxylate–ene reaction catalyzed by chiral titanium complexes . . ." Ca 110:113879, 1989.

*Primary Examiner*—Ceila Chang
*Attorney, Agent, or Firm*—George W. Johnston; William H. Epstein; John P. Parise

[57] ABSTRACT

A process manufactures of a compound of formula:

and unique intermediates.

20 Claims, No Drawings

PROCESS FOR MANUFACTURING 1-[3-CYCLOPENTYL -2(R)-[1(R)-HYDROXYCARBAMOYL)-2-(3, 4, 4-TRIMETHYL -2, 5-D IOXO-1-IMIDAZOLIDINYL) ETHYL] PROPIONYL] PIPERIDINE

CROSS REFERENCE TO RELATED APPLICATIONS

This is a divisional of application Ser. No. 08/881,262 filed Jun. 24, 1997 now abandoned.

BACKGROUND OF THE INVENTION

1. Field

The invention relates to a process for manufacturing 1-[3-cyclopentyl-2(r)-[1(r)-hydroxycarbamoyl)-2-(3,4,4-trimethyl-2,5-dioxo-1-imidazolidinyl)ethyl]propionyl]-piperidine, to a process for producing useful intermediates, and to the intermediates themselves.

2. Description

Compounds, including the compound of formula:

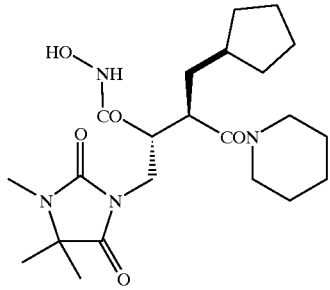

I are known from U.S. Pat. No. 5,614,625, issued Mar. 25, 1997 to Broadhurst et al., the contents of which are herein incorporated by reference. These compounds are collagenase inhibitors useful in the control or prevention of degenerative joint diseases, such as in the capacity of a cartilage protective agent.

SUMMARY OF THE INVENTION

A process for manufacturing a compound of formula:

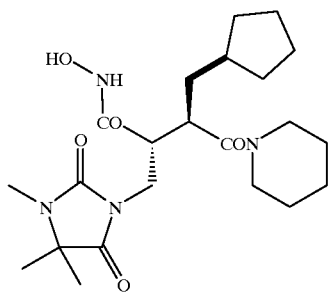

I which comprises:

a) reacting a compound of formula:

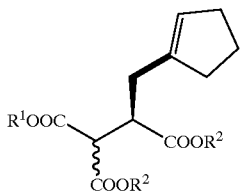

II wherein $R^2$ is a hydrolytically cleavable group and $R^1$ is methyl, ethyl, propyl, butyl, pentyl, hexyl or t-butyl, with 3-bromomethyl-1,5,5-trimethylhydantoin in the presence of a base to yield a compound of formula:

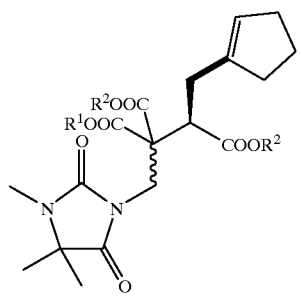

III wherein $R^1$ and $R^2$ are as defined above;

b) hydrolyzing the compound of formula III in the presence of a metal catalyst, subsequently decarboxylating the hydrolyzed compound in the presence of a base, and purifying the thus-obtained product by adding a further base which is suitable for salt formation to yield a salt of a compound of formula:

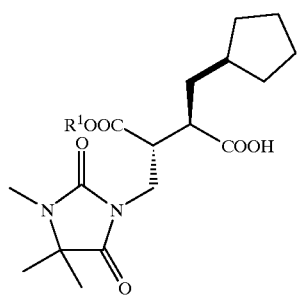

IV wherein $R^1$ is as defined above;

c) reacting the compound of formula IV with piperidine and activating the carboxylic acid to yield a compound of formula:

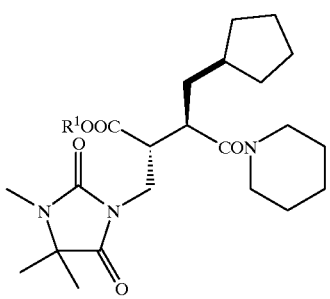

wherein R¹ is as defined above;
d) reacting the compound of formula V in which R¹ is methyl, ethyl, propyl, butyl, pentyl or hexyl with benzyl-hydroxylamine hydrochloride that has been activated by means of an alkylmagnesium halide to yield a compound of formula:

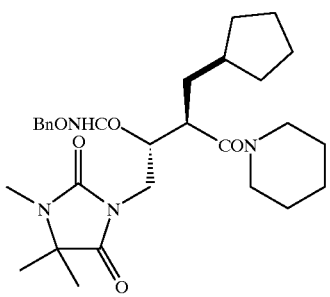

and hydrolytically cleaving the benzyl group to give the compound of formula I, or
e) cleaving the t-butyl group in the compound of formula V in which R¹ is tert-butyl with a mixture of a mineral acid and (i) a carboxylic acid, (ii) a carboxylic acid ester, or (iii) a mixture of a carboxylic acid and a carboxylic acid ester,
or cleaving the ester group in the compound of formula V in which R¹ is methyl, ethyl, propyl, butyl, pentyl or hexyl with an alkali or alkaline earth metal hydroxide
to yield a compound of formula:

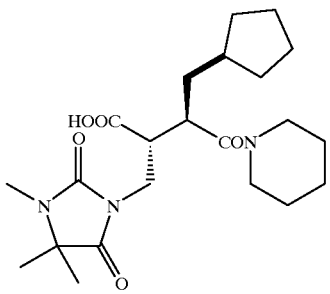

and either
(1) subsequently reacting the compound of formula VI with benzylhydroxylamine hydrochloride with the addition of an activating agent to yield the compound VII and hydrolytically cleaving the benzyl group in compound of formula VII to yield the compound of formula I,
or (2) reacting the compound of formula VI with trimethylsilyl-hydroxylamine or tetrahydropyranyl-hydroxylamine and cleaving the trimethylsilyl or tetrahydropyranyl group to yield the compound of formula I.

5. A process for the preparing a compound of formula:

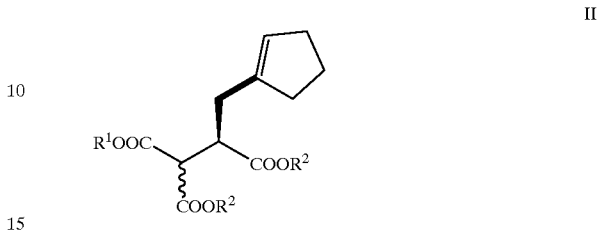

wherein R¹ is methyl, ethyl, propyl, butyl, pentyl, hexyl or t-butyl and R² is a hydrolytically cleavable group,
which comprises:
a) reacting a compound of formula:

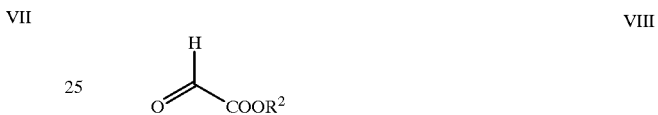

with methylenecyclopentane in the presence of catalytic amounts of (R)-binaphthyloxytitanium catalyst to yield a compound of formula:

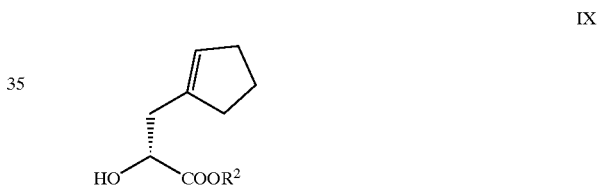

wherein R² is a hydrolytically cleavable group;
b) activating a compound of formula IX with a sulphonyl halide R³—SO₂—X, wherein R³ is trifluoromethyl, phenyl, phenyl substituted with nitro or phenyl substituted with halogen, and X is halogen, to yield a compound of formula:

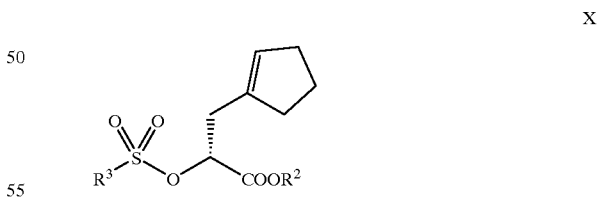

wherein R² and R³ are as above;
and
c) reacting, in the presence of a base, a compound of formula X with a compound of formula:

wherein R² is as above and R¹ is methyl, ethyl, propyl, butyl, pentyl, hexyl or t-butyl, to yield a compound of formula II.

DETAILED DESCRIPTION OF THE INVENTION

The subject invention will now be described in terms of its preferred embodiments. These embodiments are to aid in understanding the invention, but are not to be construed as limiting.

The present invention is concerned with a process for the manufacture of a compound of formula I

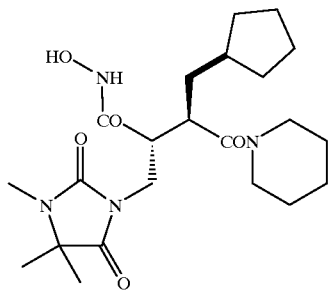

I by carrying out the following steps:

a) reaction of a compound of formula II

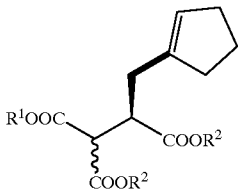

II wherein $R^2$ signifies a hydrogenolytically cleavable group and $R^1$ signifies methyl, ethyl, propyl, butyl, pentyl, hexyl or t-butyl, with 3-bromomethyl-1,5,5-trimethylhydantoin in the presence of a base to give a compound of formula III

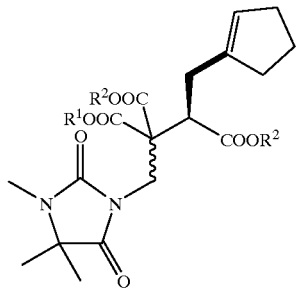

III wherein $R^1$ and $R^2$ have the significances previously defined, b) hydrogenolysis of compound III in the presence of a metal catalyst, subsequent decarboxylation in the presence of a base and purification of the thus-obtained product by addition of a further base which is suitable for salt formation to give a compound of formula IV

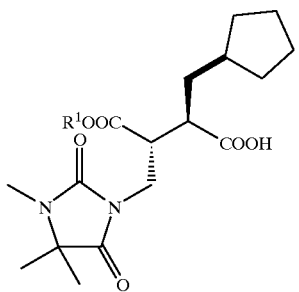

IV wherein $R^1$ is as defined above, which is obtained as a salt, c) reaction of a compound of formula IV with piperidine with activation of the carboxylic acid to give a compound of formula V

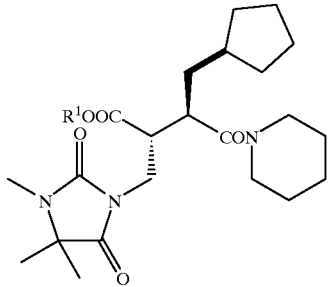

V wherein $R^1$ has the significance given above, d) reaction of a compound of formula V in which $R^1$ signifies methyl, ethyl, propyl, butyl, pentyl or hexyl with benzylhydroxylamine hydrochloride activated by means of an alkylmagnesium halide to give compound VII

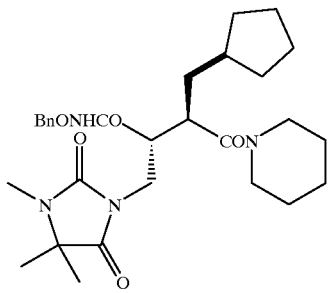

VII and hydrogenolytic cleavage of the benzyl group to give compound I, or e) cleavage of the t-butyl group in a compound of formula V in which $R^1$ signifies tert-butyl with a mixture of a mineral acid and a carboxylic acid and/or a carboxylic acid ester, or cleavage of the ester group of a compound of formula V in which $R^1$ signifies methyl, ethyl, propyl, butyl, pentyl or hexyl with an alkali or alkaline earth metal hydroxide to give compound VI

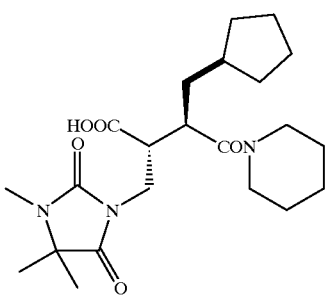

VI and either
subsequent reaction of compound VI with benzylhydroxylamine hydrochloride with the addition of an activating agent to give compound VII and hydrogenolytic cleavage of the benzyl group in compound VII to give compound I,
or
reaction of compound VI with trimethylsilyl-hydroxylamine or tetrahydropyranyl-hydroxylamine and cleavage of the trimethylsilyl or tetrahydropyranyl group according to methods known per se to give compound I.

Compound I is known and is described, for example, in U.S. Pat. No. 5,614,625, which corresponds to European Publication No. EP 0 684 240 A1. The compound has valuable pharmacological properties and can accordingly be used for the treatment and prevention of illnesses.

In accordance with the present invention a compound of formula I can be obtained, inter alia, by the purification of an intermediate via salt formation and an improved cleavage of the selected ester groups in a purer form and in a higher yield than according to the process described in the state of the art.

The term "hydrogenolytically cleavable group" denoted by $R^2$ signifies a group which can be cleaved off using methods known to a person skilled in the art, such as, for example, using hydrogen and a noble metal catalyst. Ester groups which are cleavable in this manner are e.g. the phenacyl ester, diphenylmethyl ester, p-methoxybenzyl ester or benzyl ester. Preferably, $R^2$ is benzyl in any of the compounds described hereinbefore or hereinafter.

The term "lower" denotes residues having a maximum of 7, preferably a maximum of 4, carbon atoms. The term "alkyl" denotes straight-chain or branched, saturated hydrocarbon residues such as methyl, ethyl, propyl, isopropyl, n-butyl and t-butyl.

All temperatures are in degrees Celsius.

The alkylation of the triester II with 3-bromomethyl-1,5,5-trimethylhydantoin is effected by firstly deprotonizing the triester with a base such as an alkali or alkaline earth metal hydroxide or alkoxide or a metal hydride, preferably sodium hydride, in a solvent such as an ether, e.g. 1,2-dimethoxyethane, or a sulphoxide, e.g. dimethyl sulphoxide, or an ester, e.g. ethyl acetate, or a formamide, preferably dimethylformamide, at a temperature of 0° to 100°, preferably 10° to 30°, and reacting the hydantoin with the triester II in the same solvent. Conveniently, the metal malonate is added to 3-bromomethyl-1,5,5-trimethylhydantoin at a temperature of −20° to 50°, preferably at 0° to 10°.

The 3-bromomethyl-1,5,5-trimethylhydantoin required for the reaction with the triester II can be obtained by bromomethylating 1,5,5-trimethylhydantoin. For this purpose, 1,5,5-trimethylhydantoin is conveniently reacted with hydrogen bromide in acetic acid at a temperature between 20° and 100°, preferably at about 80°. The trimethylhydantoin can be obtained according to methods known per se (H. Heimgartner et al., Helv. Chim. Acta 75, 1251 (1992)).

A compound of formula II can be obtained according to the methods described below.

The debenzylation and hydrogenation of the double bond of the triester III, obtained after alkylation with the hydantoin, is effected in the presence of usual noble metal catalysts such as e.g. palladium or platinum, especially palladium, conveniently on carriers such as Alox, barium sulphate or charcoal, the use of e.g. 5% Pd on charcoal is preferred, in the presence of a solvent such as a hydrocarbon, e.g. toluene, or a halogenated hydrocarbon such as methylene chloride or an ester such as ethyl acetate or an ether such as t-butyl methyl ether or preferably an alcohol, particularly i-propanol, at a temperature of 20° to 100°, preferably 20 to 30°.

The subsequent decarboxylation is effected without isolation of the diacid, formed as an intermediate, in the presence of a base such as e.g. an alkylamine, preferably a trialkylamine such as N-methylmorpholine, and an aprotic solvent such as a hydrocarbon, e.g. toluene, or a halogenated hydrocarbon such as chloroform or an ether such as diisopropyl ether or an ester such as ethyl acetate or preferably isopropyl acetate at a temperature of 40° to 140°, preferably at 80° to 90°. The combined use of N-methylmorpholine as the base and isopropyl acetate as the solvent yields an especially good (2R,3R):(2R,3S) isomer ratio of 85:15.

The purification of the acid is effected by salt formation with the addition of a further alkylamine, particularly with (+)-pseudoephedrine or ethanolamine, in the same solvent used for the decarboxylation. By this means, a chemically and optically pure material of formula IV is obtained as a salt.

For the reaction with piperidine, the salt is firstly converted into the free acid by partition between a solvent, preferably a solvent which is also suitable for the subsequent coupling, such as e.g. an ester, preferably ethyl acetate, and a mineral acid such as e.g. hydrochloric acid. The organic phase is dried and used for the amide formation.

The amide formation from the acid of formula IV with piperidine with activation of the carboxylic acid to give a compound of formula V can be effected according to coupling methods known per se, such as e.g. via the acid chloride, via the mixed anhydride, via an active ester or, preferably, via a mixed sulphonic acid anhydride. Thereby, water-removing agents such as a sulphonyl halide, preferably methane-sulphonyl chloride, or a carbodiimide, preferably dicyclohexylcarbodiimide, are used in the presence of stoichiometric or catalytic amounts of alcohols which form active esters, such as e.g. N-hydroxysuccinimide, N-hydroxybenzotriazole or preferably N-hydroxy-2-pyridone, in a solvent such as a ketone, e.g. methyl ethyl ketone, or an ether, e.g. t-butyl methyl ether, or a hydrocarbon, e.g. toluene, or a halogenated hydrocarbon, e.g. methylene chloride, or an ester, preferably ethyl acetate, at a temperature of 0 to 80°, preferably 10 to 25°.

The direct conversion of an ester of formula V in which $R^1$ signifies methyl, ethyl, propyl, butyl, pentyl or hexyl, preferably methyl, into the benzyl hydroxamate VII is effected by activating the O-benzylhydroxylamine hydrochloride with an alkylmagnesium halide, preferably i-propylmagnesium chloride, in the presence of the ester V in a solvent such as an ether, e.g. t-butyl methyl ether or, preferably, THF, at a temperature of −70° to 50°, preferably −20° to 0°.

The cleavage of the t-butyl group from a compound of formula V in which $R^1$ signifies tert-butyl to give compound VI is effected in the presence of a mineral acid such as e.g. aqueous phosphoric or sulphuric acid, preferably hydrochloric acid or hydrobromic acid, and an organic carboxylic acid, preferably acetic acid, at a temperature of 0 to 100°, preferably 0–22°. Instead of being carried out in a carboxylic acid, the cleavage can also be carried out in an ester of a carboxylic acid or a mixture of carboxylic acid and carboxylic acid ester. Suitable carboxylic acid esters are methyl, ethyl or isopropyl acetate, preferably ethyl acetate. HBr in a mixture of acetic acid/ethyl acetate is used as the preferred cleavage method. Furthermore, the cleavage using an acid can also be effected in another suitable organic solvent. Suitable organic solvents are methylene chloride or toluene.

The hydrolysis of an ester group of a compound of formula V in which $R^1$ signifies methyl, ethyl, propyl, butyl, pentyl or hexyl, preferably methyl, to give compound VI is effected in the presence of an alkali or alkaline earth metal hydroxide such as barium, calcium, sodium or potassium hydroxide, preferably potassium hydroxide, in a solvent such as an alcohol, e.g. i-propanol, or water with an organic solvent such as an ether, e.g. t-butyl methyl ether, or preferably THF, at a temperature of 0 to 100°, preferably 30 to 50°. Preferably, the compounds of formulae II–V are used in the form of the t-butyl ester.

The conversion of compound VI into the benzyl hydroxamate VII is effected using benzylhydroxylamine hydrochloride and an activating agent in an analogous manner to that described above for the amide formation from the acid with piperidine. Especially referred activating agents are carbodiimides, e.g. dicyclohexylcarbodiimide, or an isocyanide, e.g. t-butyl isocyanide, preferably 2-morpholino-ethyl isocyanide, in the presence of stoichiometric or catalytic amounts of alcohols which form active esters, such as e.g. N-hydroxysuccinimide, N-hydroxybenzotriazole or preferably N-hydroxy-2-pyridone. The use and preparation of such isocyanides is described in EP 29 909 B1.

The debenzylation of compound VII to compound I is effected in an organic solvent using hydrogen in the presence of a metal catalyst. Suitable solvents are $C_1$–$C_6$ alcohols, preferably methanol or ethanol. Platinum or palladium can be used as the metal catalysts, conveniently on a carrier material such as aluminium oxide, barium sulphate or charcoal. Palladium on charcoal or barium sulphate is a preferred catalyst. Temperature and pressure are not critical and can be selected within a wide range. Preferably, the hydrogenation is carried out at room temperature and 1–10 bar.

The introduction of the hydroxylamine group by means of O-trimethylsilylhydroxylamine is effected with activating agents known per se, such as carbodiimides, e.g. dicyclohexylcarbodiimide, or an isocyanide, e.g. t-butyl isocyanide, preferably 2-morpholino-ethyl isocyanide, in the presence of stoichiometric or catalytic amounts of alcohols which form active esters, such as e.g. N-hydroxysuccinimide, N-hydroxybenzotriazole or preferably N-hydroxy-2-pyridone, in a solvent such as an ether, e.g. t-butyl methyl ether, or a hydrocarbon, e.g. toluene, or a halogenated hydrocarbon or an ester, preferably methylene chloride or, respectively, ethyl acetate at a temperature of 0 to 80°, preferably 10 to 25°. It has unexpectedly been found that in the case of aqueous working-up the TMS protecting group is cleaved off smoothly and the target product I can be obtained in high yield and purity without isolation of the TMS-protected intermediate.

In a preferred embodiment compound I is manufactured from compound V via compound VI, i.e. not via step d) but via the alternative step e) where $R^1$ signifies t-butyl, followed by subsequent reaction of compound VI with trimethylsilyl hydroxylamine The present invention is also concerned with a process for the preparation of a compound of formula II which can be used as an educt for the synthesis of compound I. In a preferred embodiment the two processes for the production of compounds I and II are combined in accordance with the present invention.

The process for the preparation of a compound of formula II

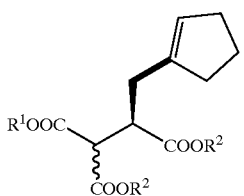

II wherein $R^1$ signifies methyl, ethyl, propyl, butyl, pentyl, hexyl or tert-butyl and $R^2$ signifies a hydrogenolytically cleavable group, comprises the following steps:

a) reaction of a glyoxylic acid derivative of formula VIII

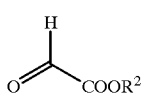

VIII with methylcyclopentane in the presence of catalytic amounts of a (R)-binaphthyloxytitanium catalyst to give a compound of formula IX

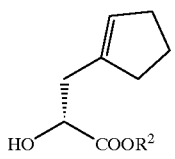

IX wherein $R^2$ represents a hydrogenolytically cleavable group, b) activation of a compound of formula IX with a sulphonyl halide $R^3$—$SO_2$—X, wherein $R^3$ signifies trifluoromethyl or phenyl optionally substituted by nitro or halogen and X signifies halogen, to give a compound of formula X

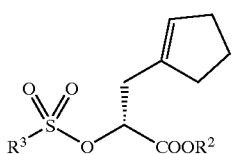

X wherein $R^2$ and $R^3$ have the previously given significances, and c) reaction of a compound of formula X with a malonic acid derivative of formula XI in the presence of a base

wherein R² has the foregoing significance and R¹ signifies methyl, ethyl, propyl, butyl, pentyl, hexyl or t-butyl, to give a compound of formula II.

The term "binaphthyloxytitanium catalyst" means a catalyst in which further ligands at the titanium of the binaphthyloxytitanium nucleus stem from the halide group, preferably chloride or bromide, or in which the further ligand can be another binaphthyloxytitanium unit. Such catalysts are described in EP 353 053 A2 and EP 676 404 A2 under formulae (IV) and (I), respectively.

Preferably, the glyoxylate-ene reaction of a compound of formula VIII with methylenecyclopentane to give the hydroxyester IX is effected with (R)-binaphthyloxytitanium dibromide or dichloride, produced in situ, according to methods known per se [Mikami et al. in J. Am. Chem. Soc. 112, 1990, 3949–3954] in a solvent such as a ketone, e.g. methyl ethyl ketone, or an ether, e.g. t-butyl methyl ether, or a hydrocarbon, e.g. toluene, or a halogenated hydrocarbon, preferably methylene chloride, at −70° to 35°, preferably 10 to 25°. A glyoxylate derivative of formula VIII in which R² is benzyl is preferably used. Methylenecyclopentane is commercially available or can be prepared in a known manner (J. M. Conia, J. C. Limasset, Bul. Soc. Chim. Fr. 1939, (1967)). Benzyl glyoxylate can also be obtained in a known manner (J. E. Bishop, J. F. O'Connell, H. Rapoport, J. Org. Chem. 56, 5079 (1991)). Other glyoxylate derivatives which can be used in the present process can be prepared according to the procedure described in Synthesis p. 544 (1972).

A high enantiomeric excess for IX can be achieved in spite of the use of a sterically demanding substituent in the R² position. The results described in the state of the art point rather to the use of small residues such as, for example, methyl. Further, it has been unexpectedly found in the case of the present reaction that the enantiomer excess (ee) was especially high (about 98%) when the reaction is carried out at room temperature. Temperatures of below 0° C. are indicated and temperatures of −30° C. are used in the state of the art for a similar reaction.

For the formation of the sulphonate X, isolated hydroxyester can be used or, conveniently, hydroxyester remaining in solution can be used directly. The reaction of the hydroxyester with a sulphonyl halide (R³—SO₂—X) is effected in the presence of a base such as a lower-alkylamine, preferably triethylamine, in an aforementioned solvent, preferably methylene chloride, at −70° to +70°, preferably at −20 to −10°. An especially preferred sulphonyl halide is o-nitrobenzenesulphonyl chloride, the ester of which can be crystallized in high optical purity (>99.9%), especially when the hydroxybenzyl ester is used in the reaction.

The alkylation of sulphonate X with the malonate (R¹O₂C—CH₂—COOR²) XI is performed by firstly deprotonizing the malonate with a base such as an alkali or alkaline earth metal hydroxide or alkoxide or a metal hydride, preferably sodium hydride, in a solvent such as an ether, e.g. 1,2-dimethoxyethane, or a sulphoxide, e.g. dimethyl sulphoxide, or an ester, e.g. ethyl acetate, or a formamide, preferably dimethylformamide, at a temperature of 0° at 100°, preferably 10 to 25°, and reacting the metal malonate with the sulphonate in the same solvent at a temperature of 0° to 100°, preferably at 10 to 20°. The malonate derivatives themselves can be obtained in a manner known per se by the stepwise derivatization of malonic acid. R¹ is preferably t-butyl in the malonate of formula XI.

The novel intermediates are also objects of the present invention. These are especially:

compounds of formula II, especially
dibenzyl (2R,3R)- and (2S,3R)-2-tert-butoxycarbonyl-3-cyclopent-1-enylmethyl-succinate and
dibenzyl (2R,3R)- and (2S,3R)-2-methoxycarbonyl-3-cyclopent-1-enylmethyl-succinate;
compounds of formula III, especially
dibenzyl (2R,3R)- and (2S,3R)-2-tert-butoxycarbonyl-3-cyclopent-1-enylmethyl-2-(3,4,4-trimethyl-2,5-dioxo-imidazolidin-1-yl-methyl)-succinate and
dibenzyl (2R,3R)- and (2S,3R)-2-methoxycarbonyl-3-cyclopent-1-enylmethyl-2-(3,4,4-trimethyl-2,5-dioxo-imidazolidin-1-yl-methyl)-succinate;
compounds of formula IV, especially
4-tert-butyl-2(R)-(cyclopentylmethyl)-3(R)-[(3,4,4-trimethyl-2,5-dioxo-1-imidazolidinyl)methyl]-succinic acid and
4-methyl-2(R)-(cyclopentylmethyl)-3(R)-(3,4,4-trimethyl-2,5-dioxo-1-imidazolidinyl)methyl]-succinic acid and their salts with (+)-pseudoephedrine or ethanolamine;
compounds of formula V, especially
1-[2(R)-[1(R)-(methoxycarbonyl)-2-(3,4,4-trimethyl-2,5-dioxo-1-imidazolidinyl)ethyl]-3-cyclopentylpropionyl] piperidine and
1-[2(R)-[1(R)-(tert-butoxycarbonyl)-2-(3,4,4-trimethyl-2,5-dioxo-1-imidazolidinyl)ethyl]-3-cyclopentylpropionyl] piperidine;
1-[2(R)-[1(R)-carboxy-2-(3,4,4-trimethyl-2,5-dioxo-1-imidazolidinyl)ethyl]-3-cyclopentylpropionyl) piperidine;
1-[2(R)-[1(R)-(benzyloxycarbamoyl)-2-(3,4,4-trimethyl-2,5-dioxo-1-imidazolidinyl)ethyl]-3-cyclopentylpropionyl)piperidine;
compounds of formula IX, especially benzyl (R)-3-cyclopent-1-enyl-2-hydroxy-propionate; and
compounds of formula X, especially benzyl (R)-3-cyclopent-1-enyl-2-(2-nitro-phenylsulphonyloxy)-propionate.

The intermediates of the present invention can be used for the manufacture of a compound of formula I or II. Compounds of formulas II, V and IX are especially suitable.

The following Examples illustrate the present invention without being limiting.

EXAMPLE 1

6.60 g of methylene-cyclopentane were added at 220 to 11 ml of catalyst suspension consisting of 135 mg (R)-(+)-1,1'-binaphthol, 153 mg of diisopropoxytitanium (IV) dibromide, 0.9 ml of toluene, 8 ml of methylene chloride and 2.8 g of molecular sieve (4, powder, Aldrich), prepared according to K. Makami et al., Org. Synth. 71, 14 (1993) and subsequently treated during 80 min. with a heat-treated solution consisting of 18.55 g of benzyl glyoxylate and 48 ml of toluene (solution initially heated at reflux for 16 hrs. and cooled to 22°). The orange suspension was stirred for 3 hrs., again treated with 11 ml of the catalyst suspension described above and stored at +4° overnight. The suspension was filtered, the filtrate containing the resulting benzyl (R)-3-cyclopenten-1-enyl-2-hydroxy-propionate was treated with 23.0 g of o-nitrobenzenesulphonyl chloride and the solution was cooled to −15° and treated with 23.9 g of triethylamine during 45 min. After 5 hrs. at −15° the mixture was made acid with 150 ml of 1N sulphuric acid and extracted with methylene chloride. The methylene chloride phases were washed with water, dried and concentrated. The residue was recrystallized from 170 ml of ethyl acetate and the crystallizate was dried, there being obtained 19.2 g (55%) of pure benzyl (R)-3-cyclopent-1-enyl-2-(2-nitrophenylsulphonyloxy)-propionate, m.p. 122.5–124.5°. IR (KBr): 1736s (C=O), 1543s and 1370s (NO$_2$), 1380s and 1191s (SO$_3$).

EXAMPLE 2

A suspension of 21.3 g of 1,5,5-trimethylhydantoin, 5.86 g of paraformaldehyde and 34 ml of hydrogen bromide in acetic acid (33%) was heated to 80° for 2 hrs., again treated with 7.9 ml of hydrogen bromide in acetic acid and heated for a further 2.5 hrs. The solution was cooled to 0°, diluted with 100 ml of methylene chloride and subsequently treated at 0° with 100 ml of ice-cold water. The methylene chloride phase was washed with water, dried and concentrated. The residue was crystallized from t-butyl methyl ether/hexane and the crystallizate was dried, there being obtained 30.9 g (88%) of pure 3-bromomethyl-1,5,5-trimethylhydantoin, m.p. 86–88°. IR (KBr): 1780s and 1732s (C=O).

EXAMPLE 3

A suspension of 3.17 g of NaH (55–65% in oil, firstly washed with hexane) in 30 ml of DMF was treated with a solution of 18.02 g of benzyl t-butylmalonate in 30 ml of DMF and stirred at 22° for 30 min. The solution was treated portionwise with 31.06 g of o-nisylate from Example 1, stirred at 22° for 6 hrs., a further 6.21 g of o-nisylate were added and the mixture was stirred at 22° for 22 hrs. The red solution was diluted at 10° with 100 ml of hexane and 200 ml of water, stirred at 10° for 1 hr. and excess o-nisylate was removed by filtration. The organic phase of the filtrate was washed with water, dried and concentrated. The residue contained 35 g of a 1:1 mixture of the triester dibenzyl (2R,3R)- and (2S,3R)-2-tert-butyloxycarbonyl-3-cyclopent-1-enylmethyl-succinate, which was used in the next step without further purification.

EXAMPLE 4

Analogously to Example 3, from the sulphonate of Example 1 by reaction with benzyl methyl malonate there was obtained a 1:1 mixture of the triester dibenzyl (2R,3R)- and (2S,3R)-2-methyloxycarbonyl-3-cyclopent-1-enylmethyl-succinate.

EXAMPLE 5

A suspension of 3.15 g of NaH (55–65% in oil, firstly washed with hexane) in 30 ml of DMF was treated with a solution of 34.95 g of the triester mixture from Example 3 in 60 ml of DMF and stirred at 22° for 30 min. The resulting solution was added dropwise at 0° to a solution consisting of 20.2 g of 2-bromomethyl-1,5,5-trimethylhydantoin from Example 2 and 30 ml of DMF and stirred at 0° for 4 hrs. The suspension was diluted with 300 ml of cyclohexane and 300 ml of water at 0° and the organic phase was washed with 0.1N hydrochloric acid, with 0.1N sodium hydroxide solution and with water, dried and concentrated. The residue contained 47.3 g of a mixture of dibenzyl (2R,3R)- and (2S,3R)-2-tert-butoxycarbonyl-3-cyclopent-1-enylmethyl-2-(3,4,4-trimethyl-2,5-dioxo-imidazolidin-1-yl-methyl)-succinate, which was used in the next step without further purification.

EXAMPLE 6

Analogously to Example 5, from the product of Example 4 by reaction with 2-bromomethyl-1,5,5-trimethylhydantoin there was obtained the corresponding 1:1 mixture of dibenzyl (2R,3R)- and (2S,3R)-2-methoxycarbonyl-3-cyclopent-1-enylmethyl-2-(3,4,4-trimethyl-2,5-dioxo-imidazolidin-1-yl-methyl)-succinate.

EXAMPLE 7

A suspension consisting of 46.9 g of the hydantoyl triester from Example 5 and 9.38 g of Pd/C (5%) in 470 ml of i-PrOH was hydrogenated at 22–33°/1 bar for 24 h. The suspension was filtered, the filtrate was concentrated completely and the residue was dissolved in 460 ml of i-propyl acetate. The solution was treated with 7.2 g of N-methylmorpholine, heated at reflux for 4 hrs., treated with 11.7 g of (+)-pseudoephedrine and cooled to 22°. After 4 hrs. at 22° the mixture was filtered and the crystallizate was dried, there being obtained 24.5 g (60%) of pure ephedrine salt of 4-tert-butyl-2(R)-(cyclopentylmethyl)-3(R)-[(3,4,4-trimethyl-2,5-dioxo-1-imidazolidinyl)methyl]-succinic acid, m.p. 169–170°. IR (KBr): 3234 m, br. (NH, OH), 1771m and 1720s, br. (C=O).

EXAMPLE 8

Analogously to Example 7, by reacting the methyl derivative from Example 6 there was obtained as the product the ephedrine salt of 4-methyl-2(R)-(cyclopentylmethyl)-[3(R)-(3,4,4-trimethyl-2,5-dioxo-1-imidazolidinyl)methyl]-succinic acid, m.p. 141–143°, in 44–50% yield. IR (KBr): 3433m, br. (NH, OH), 1770m and 1735s and 1714s (C=O).

EXAMPLE 9

A solution of 8.64 g of ephedrine salt from Example 7 in 50 ml of ethyl acetate was shaken with 50 ml of 2N hydrochloric acid, the organic phase was washed with water and the aqueous phases were back-extracted with 25 ml of ethyl acetate. The combined ethyl acetate phases were dried, treated in succession at 22° with 0.32 g of N-hydroxy-2-pyridone, 1.22 g of piperidine and a solution consisting of 3.24 g of dicyclohexylcarbodiimide and 17.5 ml of ethyl acetate and stirred for 16 hrs. The suspension was stirred at 0° for 1 hr., filtered and the filtrate was washed with sodium bicarbonate solution and water, dried and concentrated. The residue contained 7.8 g of 1-[2(R)-[1(R)-(tert-butoxycarbonyl)-2-(3,4,4-trimethyl-2,5-dioxo-1-imidazolidinyl)ethyl]-3-cyclopentylpropionyl]piperidine, which was used in the next step without further purification.

EXAMPLE 10

Analogously to Example 9, by reaction of the ephedrine salt from Example 8 there was obtained 1-[2(R)-[1(R)-(methoxycarbonyl)-2-(3,4,4-trimethyl-2,5-dioxo-1-imidazolidinyl)ethyl]-3-cyclopentylpropionyl]piperidine, which was used in the next step without further purification.

EXAMPLE 11

0.84 ml of 37% hydrochloric acid was added to a solution of 475 mg of t-butyl ester from Example 9 in 1.3 ml of acetic acid and the mixture was stirred at 22° for 1 hr. The solution was diluted with 3 ml of water and extracted with methylene chloride. The extracts were washed with water, dried and concentrated. The residue contained 393 mg of pure 1-[2(R)-[1(R)-carboxy-2-(3,4,4-trimethyl-2,5-dioxo-1-imidazolidinyl)ethyl]-3-cyclopentylpropionyl)piperidine. IR (KBr): 1769m and 1714s (C=O).

Alternatively, 12.2 ml of 33% hydrobromic acid in acetic acid were added to a solution of 8.30 g of t-butyl ester from Example 9 in 50 ml of ethyl acetate at 0° and the mixture was stirred at 0° for 3½ hrs. The organic phase was washed neutral with water, dried and concentrated. The residue contained 7.3 g of pure 1-[2(R)-[1(R)-carboxy-2-(3,4,4-trimethyl-2,5-dioxo-1-imidazolidinyl)ethyl]-3-cyclopentylpropionyl)-piperidine.

EXAMPLE 12

A solution of 1.78 g of methyl ester from Example 10 in 3 ml of THF was treated with a solution of 0.69 g of KOH in 6.1 ml of water and stirred vigorously at 0° for 5 hrs. and at 40° for 10 hrs. The mixture was adjusted to pH 2 with dilute hydrochloric acid and treated with 8 ml of THF and 6 ml of saturated sodium chloride solution. The THF phase was washed with semi-concentrated sodium chloride solution, dried and concentrated. The residue contained 1.68 g of about 95% pure 1-[2(R)-[1(R)-carboxy-2-3,4,4-trimethyl-2,5-dioxo-1-imidazolidinyl)ethyl]-3-cyclopentylpropionyl)piperidine VI. IR KBr): 1769m and 1714s (C=O).

EXAMPLE 13

0.74 g of N-ethylmorpholine, 0.60 g of hydroxybenzotriazole hydrate and 0.75 g of N-ethyl-N'-(3-dimethylaminopropyl)-carbodiimide were added at 0° in succession to a solution of 1.38 g of 1-[2(R)-[1(R)-carboxy-2-(3,4,4-trimethyl-2,5-dioxo-1-imidazolidinyl)ethyl]-3-cyclopentylpropionyl)piperidine VI in 13 ml of methylene chloride and the mixture was stirred at 0° for 20 min. The reaction mixture was treated with 0.45 g of N-ethylmorpholine and 0.63 g of O-benzylhydroxylamine hydrochloride and stirred at 0° for 30 min. and at 22° for 17 hrs. The solution was diluted with 13 ml of methylene chloride, washed with sodium bicarbonate solution and dilute hydrochloric acid, dried and concentrated. The residue was crystallized from ethyl acetate/hexane and the crystallizate was dried, there being obtained 1.26 g (73%) of pure 1-[2(R)-[1(R)-(benzyloxycarbamoyl)-2-(3,4,4-trimethyl-2,5-dioxo-1-imidazolidinyl)ethyl]-3-cyclopentylpropionyl)piperidine VII, m.p. 138–140°.

Alternatively, 3.86 g of 2-morpholino-ethyl isocyanide were added to a suspension of 10.54 g of the acid from Example 11 and 3.06 g of N-hydroxy-2-pyridone in 110 ml of methylene chloride at 22° and the mixture was stirred for 2 hrs. The solution was treated with 3.39 g of O-benzylhydroxylamine and stirred for 5 hrs. The reaction mixture was washed with dilute hydrochloric acid, NaHCO₃ solution and water, dried and concentrated. After recrystallization from methylene chloride the residue yielded 11.19 g (85%) of pure benzyl hydroxamate VII, m.p. 140–142°.

EXAMPLE 14

A solution of 1.10 g of methyl ester from Example 10 and 568 mg of O-benzylhydroxylamine hydrochloride in 7 ml of THF was treated at −20° with 3.5 ml of a 2M i-PrMgCl solution in THF and, after 1 hr. at −20°, treated with a further 1.7 ml of the Grignard reagent. After a further 2½ hrs. at −20° the mixture was treated with ammonium chloride solution and extracted with methylene chloride. The extracts were dried and concentrated. The residue was crystallized from t-butyl methyl ether/hexane and the crystallizate was dried, there being obtained 1-[2(R)-[1 (R)-(benzyloxycarbamoyl)-2-(3,4,4-trimethyl-2,5-dioxo-1-imidazolidinyl)ethyl]-3-cyclopentylpropionyl)piperidine VII, m.p. 135–137°.

EXAMPLE 15

For the debenzylation, a suspension of 5.5 g of 1-[2(R)-[1(R)-(benzyloxycarbamoyl)-2-(3,4,4-trimethyl-2,5-dioxo-1-imidazolidinyl)ethyl]-3-cyclopentylpropionyl)piperidine VII in 40 ml of ethanol and 1.7 g of Pd/C (5%) was hydrogenated at 22°/1 bar for 4 h. The suspension was filtered, the filtrate was concentrated completely and the residue was crystallized from water, there being obtained 3.9 g (85%) of pure 1-[3-cyclopentyl-2(R)-[1(R)-(hydroxycarbamoyl)-2-(3,4,4-trimethyl-2,5-dioxo-1-imidazolidinyl)ethyl]propionyl]piperidine I. MS (EI): 436 (40%).

EXAMPLE 16

0.78 g of 2-morpholino-ethyl isocyanide was added at 22° to a suspension of 2.11 g of 1-[2(R)-[1(R)-carboxy-2-(3,4, 4-trimethyl-2,5-dioxo-1-imidazolidinyl)ethyl]-3-cyclopentylpropionyl)piperidine from Example 11 and 0.61 g of N-hydroxy-2-pyridone in 21 ml of methylene chloride and the mixture was stirred for 3 hrs. The solution was treated with 0.58 g of O-trimethylsilyl-hydroxylamine and stirred for 2 hrs. The reaction mixture was washed with saturated NaHCO₃ solution and with water and evaporated. The residue was dissolved in 20 ml of t-butyl methyl ether and 0.23 ml of water, stirred for 1½ hrs. at 22°, the suspension was diluted with 10 ml of hexane, filtered and the residue was dried at 22°/11 mbar, there being obtained 1.82 g (83%) of pure 1-[3-cyclopentyl-2(R)-[1(R)-(hydroxycarbamoyl)-2-(3,4,4-trimethyl-2,5-dioxo-1-imidazolidinyl)-ethyl]propionyl]piperidine I, MS (EI): 436 (40%).

Upon reading the specification, various alternative embodiments will become obvious to the skilled artisan. These embodiments are to be considered within the scope and spirit of the invention which is only to be limited to the claims that follow and their equivalents.

What is claimed is:

1. A process for manufacturing a compound of formula:

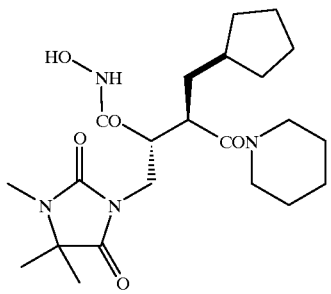

I which comprises:

a) reacting a compound of formula:

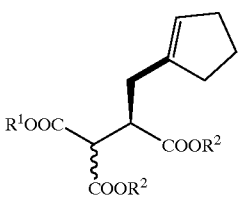

II wherein R² is a hydrolytically cleavable group and R¹ is methyl, ethyl, propyl, butyl, pentyl, hexyl or t-butyl, with 3-bromomethyl-1,5,5-trimethylhydantoin in the presence of a base to yield a compound of formula:

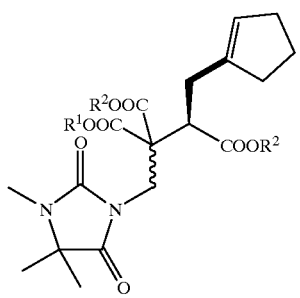

III

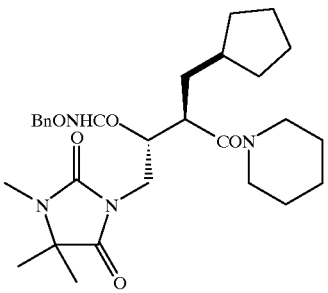

VII wherein R¹ and R² are as defined above;

b) hydrolyzing and hydrogenating the compound of formula III in the presence of a metal catalyst, subsequently decarboxylating the hydrolyzed compound in the presence of a base, and purifying the thus-obtained product by adding a further base which is suitable for salt formation to yield a salt of a compound of formula:

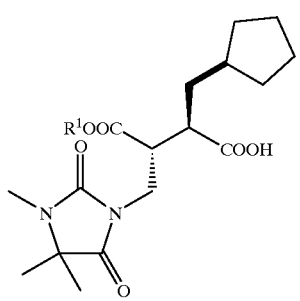

IV wherein R¹ is as defined above;

c) reacting the compound of formula IV with piperidine and activating the carboxylic acid to yield a compound of formula:

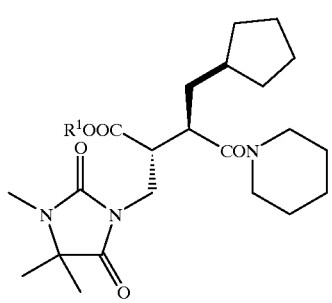

V wherein R¹ is as defined above;

d) reacting the compound of formula V in which R¹ is methyl, ethyl, propyl, butyl, pentyl or hexyl with benzylhydroxylamine hydrochloride that has been activated by means of an alkylmagnesium halide to yield a compound of formula:

and hydrolytically cleaving the benzyl group to give the compound of formula I, or e) cleaving the t-butyl group in the compound of formula V in which R¹ is tert-butyl with a mixture of a mineral acid and (i) a carboxylic acid, (ii) a carboxylic acid ester, or (iii) a mixture of a carboxylic acid and a carboxylic acid ester, or cleaving the ester group in the compound of formula V in which R¹ is methyl, ethyl, propyl, butyl, pentyl or hexyl with an alkali or alkaline earth metal hydroxide to yield a compound of formula:

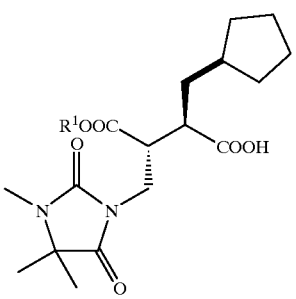

IV and either (1) subsequently reacting the compound of formula VI with benzylhydroxylamine hydrochloride with the addition of an activating agent to yield the compound VII and hydrolytically cleaving the benzyl group in compound of formula VII to yield the compound of formula I, or (2) reacting the compound of formula VI with trimethylsilyl-hydroxylamine or tetrahydropyranyl-hydroxylamine and cleaving the trimethylsilyl or tetrahydropyranyl group to yield the compound of formula I.

2. The process of claim 1, which comprises:

a) reacting a compound of formula:

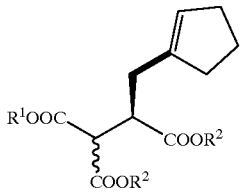
II wherein $R^2$ is a hydrolytically cleavable group and $R^1$ is methyl, ethyl, propyl, butyl, pentyl or hexyl, with 3-bromomethyl-1,5,5-trimethylhydantoin in the presence of a base to yield a compound of formula:

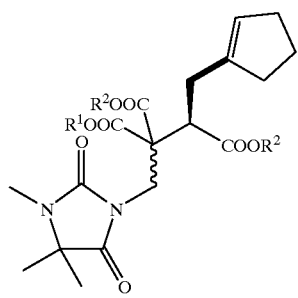
III wherein $R^1$ and $R^2$ are as defined above;

b) hydrolyzing and hydrogenating the compound of formula III in the presence of a metal catalyst, subsequently decarboxylating the hydrolyzed compound in the presence of a base, and purifying the thus-obtained product by adding a further base which is suitable for salt formation to yield a salt of a compound of formula:

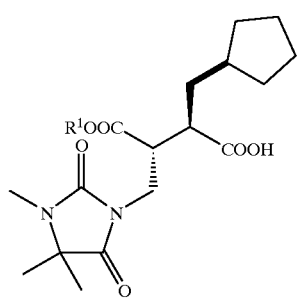
IV wherein $R^1$ is as defined above;

c) reacting the compound of formula IV with piperidine and activating the carboxylic acid to yield a compound of formula:

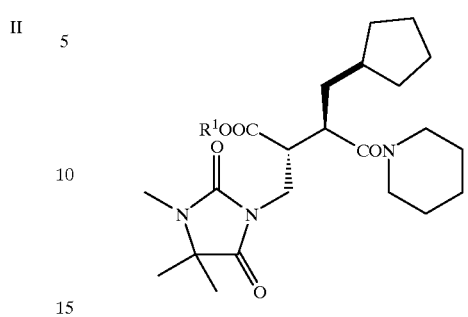
V wherein $R^1$ is as defined above;

d) reacting the compound of formula V with benzylhydroxylamine hydrochloride that has been activated by means of an alkylmagnesium halide to yield a compound of formula:

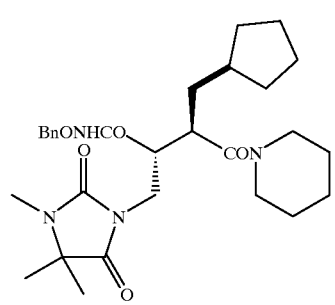
VII and e) hydrolytically cleaving the benzyl group to give the compound of formula I.

3. The process of claim 1, which comprises:

a) reacting a compound of formula:

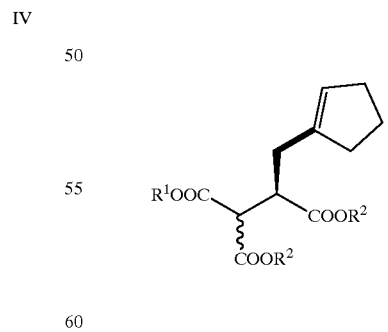
II wherein $R^2$ is a hydrolytically cleavable group and $R^1$ is methyl, ethyl, propyl, butyl, pentyl or hexyl, with 3-bromomethyl-1,5,5-trimethylhydantoin in the presence of a base to yield a compound of formula:

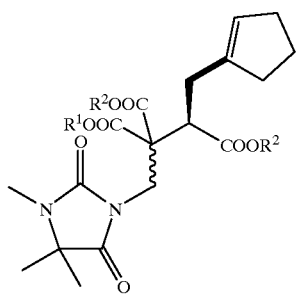

III wherein $R^1$ and $R^2$ are as defined above;

b) hydrolyzing and hydrogenating the compound of formula III in the presence of a metal catalyst, subsequently decarboxylating the hydrolyzed compound in the presence of a base, and purifying the thus-obtained product by adding a further base which is suitable for salt formation to yield a salt of a compound of formula:

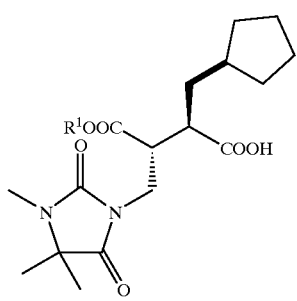

IV wherein $R^1$ is as defined above;

c) reacting the compound of formula IV with piperidine and activating the carboxylic acid to yield a compound of formula:

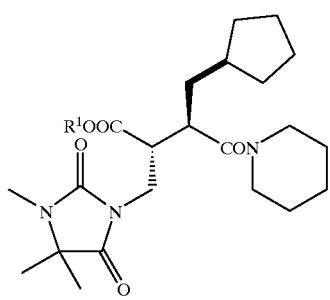

V wherein $R^1$ is as defined above;

d) cleaving the ester group in the compound of formula V with an alkali or alkaline earth metal hydroxide to yield a compound of formula:

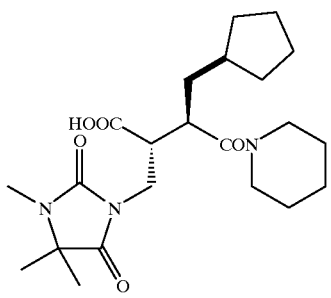

VI e) reacting the compound of formula VI with benzylhydroxylamine hydrochloride with the addition of an activating agent to yield a compound of formula:

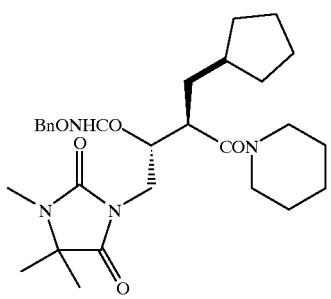

VII and f) hydrolytically cleaving the benzyl group in the compound of formula VII to yield the compound of formula I.

4. The process of claim 1, which comprises:

a) reacting a compound of formula:

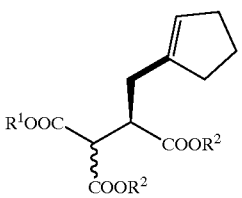

II wherein $R^2$ is a hydrolytically cleavable group and $R^1$ is methyl, ethyl, propyl, butyl, pentyl or hexyl, with 3-bromomethyl-1,5,5-trimethylhydantoin in the presence of a base to yield a compound of formula:

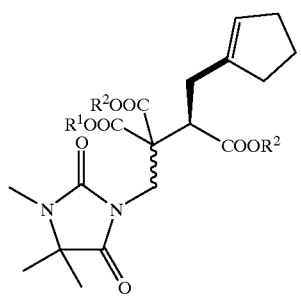

III wherein R¹ and R² are as defined above;

b) hydrolyzing and hydrogenating the compound of formula III in the presence of a metal catalyst, subsequently decarboxylating the hydrolyzed compound in the presence of a base, and purifying the thus-obtained product by adding a further base which is suitable for salt formation to yield a salt of a compound of formula:

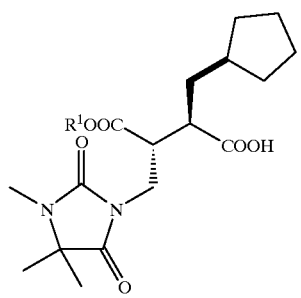

IV wherein R¹ is as defined above;

c) reacting the compound of formula IV with piperidine and activating the carboxylic acid to yield a compound of formula:

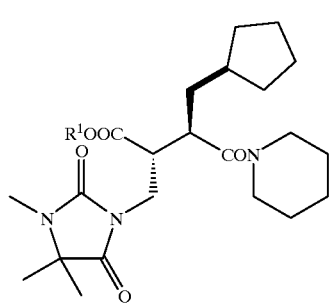

V wherein R¹ is as defined above;

d) cleaving the ester group in the compound of formula V with an alkali or alkaline earth metal hydroxide to yield a compound of formula:

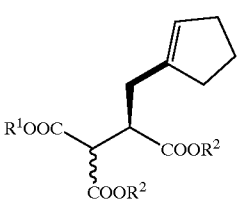

VI and e) reacting the compound of formula VI with trimethylsilyl-hydroxylamine or tetrahydropyranyl-hydroxylamine and cleaving the trimethylsilyl or tetrahydropyranyl group to yield the compound of formula I.

5. The process of claim 1, which comprises:

a) reacting a compound of formula:

II wherein R² is a hydrolytically cleavable group and
R¹ is t-butyl, with 3-bromomethyl-1,5,5-trimethylhydantoin in the presence of a base to yield a compound of formula:

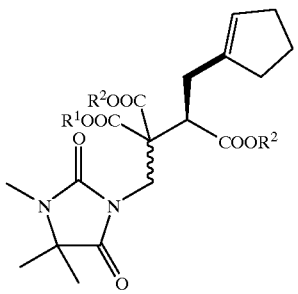

III wherein R¹ and R² are as defined above;

b) hydrolyzing and hydrogenating the compound of formula III in the presence of a metal catalyst, subsequently decarboxylating the hydrolyzed compound in the presence of a base, and purifying the thus-obtained product by adding a further base which is suitable for salt formation to yield a salt of a compound of formula:

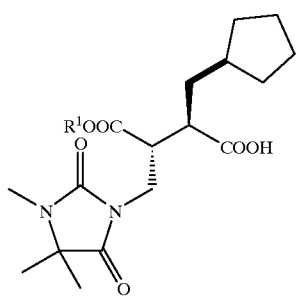

IV wherein $R^1$ is as defined above;

c) reacting the compound of formula IV with piperidine and activating the carboxylic acid to yield a compound of formula:

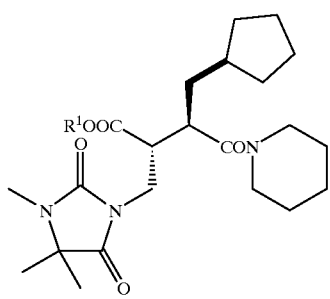

V wherein $R^1$ is as defined above;

d) cleaving the t-butyl group in the compound of formula V with a mixture of a mineral acid and (i) a carboxylic acid, (ii) a carboxylic acid ester, or (iii) a mixture of a carboxylic acid and a carboxylic acid ester, to yield a compound of formula:

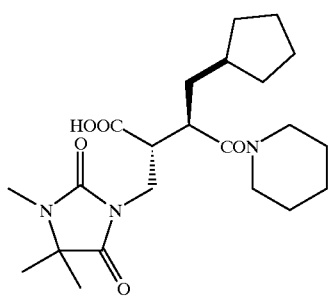

VI and e) subsequently reacting the compound of formula VI with benzylhydroxylamine hydrochloride with the addition of an activating agent to yield a compound of formula:

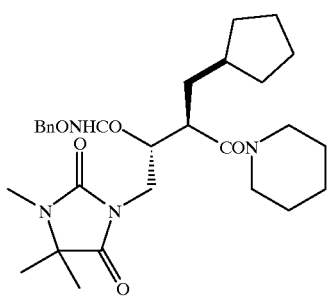

VII and f) hydrolytically cleaving the benzyl group in the compound of formula VII to yield the compound of formula I.

6. The process of claim 1, which comprises:

a) reacting a compound of formula:

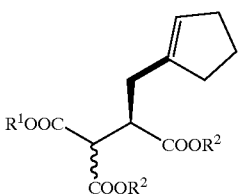

II wherein $R^2$ is a hydrolytically cleavable group and $R^1$ is t-butyl, with 3-bromomethyl-1,5,5-trimethylhydantoin in the presence of a base to yield a compound of formula:

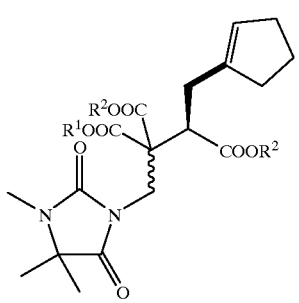

III wherein $R^1$ and $R^2$ are as defined above;

b) hydrolyzing and hydrogenating the compound of formula III in the presence of a metal catalyst, subsequently decarboxylating the hydrolyzed compound in the presence of a base, and purifying the thus-obtained product by adding a further base which is suitable for salt formation to yield a salt of a compound of formula:

wherein $R^1$ is as defined above;

c) reacting the compound of formula IV with piperidine and activating the carboxylic acid to yield a compound of formula:

V wherein $R^1$ is as defined above;

d) cleaving the t-butyl group in the compound of formula V with a mixture of a mineral acid and (i) a carboxylic acid, (ii) a carboxylic acid ester, or (iii) a mixture of a carboxylic acid and a carboxylic acid ester, to yield a compound of formula:

VI and e) reacting the compound of formula VI with trimethylsilyl-hydroxylamine or tetrahydropyranyl-hydroxylamine and cleaving the trimethylsilyl or tetrahydropyranyl group to yield the compound of formula I.

7. The process according to claim 1, wherein $R^2$ is benzyl.
8. The process according to claim 2, wherein $R^2$ is benzyl.
9. The process according to claim 3, wherein $R^2$ is benzyl.
10. The process according to claim 4, wherein $R^2$ is benzyl.
11. The process according to claim 5, wherein $R^2$ is benzyl.
12. The process according to claim 6, wherein $R^2$ is benzyl.
13. A process for the preparing a compound of formula:

II wherein $R^1$ is methyl, ethyl, propyl, butyl, pentyl, hexyl or t-butyl and $R^2$ is a hydrolytically cleavable group, which comprises:

a) reacting a compound of formula:

VIII with methylenecyclopentane in the presence of catalytic amounts of (R)-binaphthyloxytitanium catalyst to yield a compound of formula:

IX wherein $R^2$ is a hydrolytically cleavable group;

b) activating a compound of formula IX with a sulphonyl halide $R^3$—$SO_2$—X, wherein $R^3$ is trifluoromethyl, phenyl, phenyl substituted with nitro or phenyl substituted with halogen, and X is halogen, to yield a compound of formula:

X wherein $R^2$ and $R^3$ are as above; and c) reacting, in the presence of a base, the compound of formula X with a compound of formula:

$$R^1O_2CCH_2CO_2R^2 \qquad XI$$

wherein $R^2$ is as above and $R^1$ is methyl, ethyl, propyl, butyl, pentyl, hexyl or t-butyl, to yield a compound of formula I.

14. The process according to claim 13, wherein $R^2$ is benzyl.
15. The process according to claim 14, wherein the sulphonyl halide is ortho-nitrosulphonyl chloride.

16. A compound of formula:

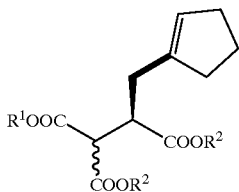

II wherein $R^1$ is methyl, ethyl, propyl, butyl, pentyl, hexyl or tert-butyl and $R^2$ is a hydrolytically cleavable group.

17. The compound of claim 16 which is dibenzyl (2R, 3R)-tert-butoxycarbonyl-3-cyclopent-1-enylmethyl-succinate, and dibenzyl (2R,3R)- and (2S,3R)-2-methoxycarbonyl-3-cyclopent-1-enylmethyl-succinate.

18. The compound of claim 16 which is dibenzyl (3S, 3R)-2-tert-butoxycarbonyl-3-cyclopent-1-enylmethyl-succinate.

19. The compound of claim 16 which is dibenzyl (2R, 3R)-2-methoxycarbonyl-3-cyclopent-1-enylmethyl-succinate.

20. The compound of claim 16 which is dibenzyl (2S, 3R)-2-methoxycarbonyl-3-cyclopent-1-enylmethyl-succinate.

* * * * *

UNITED STATES PATENT AND TRADEMARK OFFICE
CERTIFICATE OF CORRECTION

PATENT NO.    : 6,031,103
DATED         : February 29, 2000
INVENTOR(S)   : Paul Anthony Brown and Hans Hilpert Page 1 of 1

It is certified that error appears in the above-identified patent and that said Letters Patent is hereby corrected as shown below:

Claim 1, column 18,
Line 36 delete

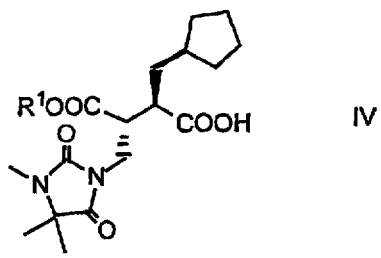

and insert

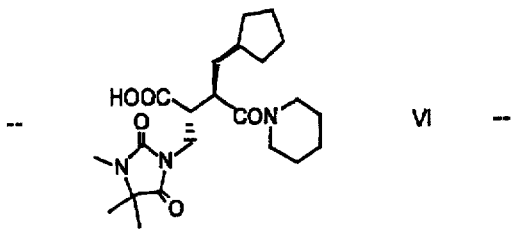

Claim 13, column 28,
Line 63, delete "formula I." and insert -- formula II. --

Signed and Sealed this

Sixteenth Day of October, 2001

Attest:

NICHOLAS P. GODICI
Attesting Officer     Acting Director of the United States Patent and Trademark Office